(12) United States Patent
Bayati

(10) Patent No.: US 6,986,882 B2
(45) Date of Patent: Jan. 17, 2006

(54) THERAPY FOR FUNCTIONAL DYSPEPSIA

(75) Inventor: Alfred Bayati, Floda (SE)

(73) Assignee: AstraZeneca AB, Sodertalje (SE)

( * ) Notice: Subject to any disclaimer, the term of this patent is extended or adjusted under 35 U.S.C. 154(b) by 217 days.

(21) Appl. No.: 10/053,279

(22) Filed: Jan. 17, 2002

(65) Prior Publication Data

US 2003/0135133 A1   Jul. 17, 2003

(51) Int. Cl.
*A61K 51/00*   (2006.01)
*A61K 49/00*   (2006.01)
(52) U.S. Cl. .......................................... 424/9.2; 424/9.1
(58) Field of Classification Search ................ 424/9.2, 424/9.1; 514/295, 469, 651, 28
See application file for complete search history.

(56) References Cited

U.S. PATENT DOCUMENTS 5,000,953 A * 3/1991 Ui et al. ...................... 424/115
5,552,398 A * 9/1996 King et al. ............ 514/214.01
5,912,235 A * 6/1999 Hoeltje et al. ................. 514/28

OTHER PUBLICATIONS

M. Nordling, "A Comparative Study of Gastric Distension in Different Rat Strains," Master of Science Thesis, University of Uppsala, Sweden, 2000.

* cited by examiner

*Primary Examiner*—Michael Hartley
(74) *Attorney, Agent, or Firm*—White & Case LLP

(57) ABSTRACT

The invention features a method of identifying a candidate drug for treating functional dyspepsia. The invention also features a method of diagnosing a patient with functional dyspepsia.

5 Claims, 7 Drawing Sheets

Figure 4(a)
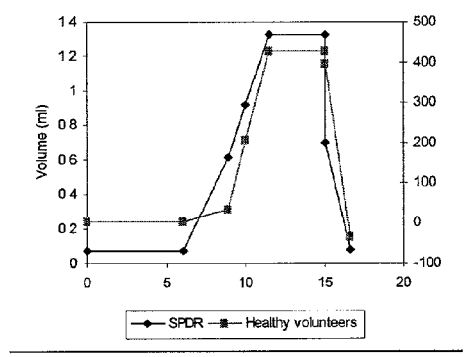
Figure 4(b)
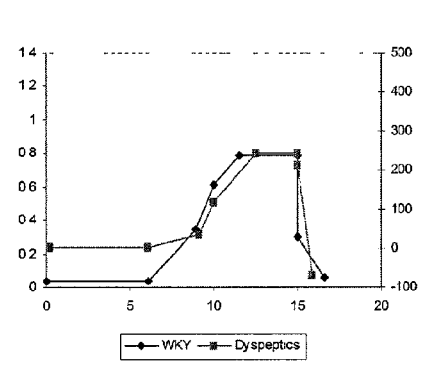
Figure 4

THERAPY FOR FUNCTIONAL DYSPEPSIA

FIELD OF THE INVENTION

The present invention relates to an animal model for functional dyspepsia (FD). Moreover, the present invention relates to a method for diagnosing a patient with functional dyspepsia.

BACKGROUND

Functional dyspepsia (FD) is a very common gastrointestinal (GI) disorder. At present there is no reliable means to diagnose this disease and diagnosis is based on symptoms presented.

Investigators working on FD have identified that many patients having FD have delayed gastric emptying and weak antral motility. Recently, studies have also shown that patients having FD have impaired accommodation of the proximal stomach to meals (Salet et al, Gut, 42:823–829, 1998, Tack et al, Gastroenterology, 115:1346–1352, 1998). Using barostat techniques and ultrasonography it has been shown that the reservoir function of the proximal stomach is abnormal in a significant proportion of FD patients. The reflex regulating the reservoir function of the stomach is called adaptive accommodation and it is thought to be mediated by both intrinsic and extrinsic (vagal) neuronal pathways. It has been suggested that abnormal vagal activity might be the reason for the impaired accommodation of the stomach in FD patients. The impaired gastric accommodation might also cause the increase in visceral sensitivity and symptoms.

There are a few reports in the literature of animal models for the use in studying pressure-volume handling in conscious animals. Bueno et al disclosed a rat model to study gastric sensitivity and measured the maximal volume at a pressure of 20 mmHg and the visceromotor response related to maximal volume (Neurogastroenterology & Motility, 10(2):157–63, 1998). Paterson et al conducted studies in dogs using barostat technique and examined the effect of different pharmacological substances on the maximum volume of the stomach (Neurogastroenterology & Motility, 12(4):301–6, 2000). No studies have been reported where the physico-mechanical properties of the stomach have been studied in detail in response to distension.

SUMMARY OF THE INVENTION

The present invention relates to an in vivo non-human animal model for FD and, more particularly, to the use of this animal model to identify candidate agents useful in the treatment of FD. The present invention also provides a method to diagnose FD in a human.

In one aspect, the invention features a method of identifying a test compound useful for the treatment of an impaired maximum gastric accommodation capacity. The method includes administering a test compound to a non-human animal identified to have an impaired maximum gastric accommodation capacity; determining the maximum gastric accommodation capacity in the animal following administration of the compound; and comparing the maximum gastric accommodation capacity of the animal before and after administration of the test compound, wherein an increase in the accommodation capacity in the animal following administration of the compound is indicative that the compound is useful for the treatment of impaired maximum gastric accommodation capacity. The non-human animal can be any animal such as a rat or a dog. In one embodiment, the rat is a Wistar Kyoto rat. The test compound can be any compound and can be administered by any route, e.g., orally.

In one embodiment, the compound is a nitrogen oxide synthase (NOS) inhibitor, a 5HT-3 agonist, a 5HT-4 antagonist, an alpha-2 agonist, a glucagon or a cholinergic agonist or antagonist.

The invention also features a compound identified by the method described above and a pharmaceutical formulation which includes the compound.

Also included within the invention is a compound identified by the method described herein in the manufacture of a medicament for the treatment of functional dyspepsia.

The invention further features a method for the treatment of functional dyspepsia including administering to a subject an effective amount of the compound identified as described above.

In another aspect, the invention features a method of diagnosing functional dyspepsia in a human. The method includes inserting a balloon into the stomach of a test human suspected of having functional dyspepsia; applying a start minimum pressure to the balloon such that the stomach of the test patient is not distended and determining the volume response; increasing the pressure in the balloon to a maximum pressure of not more than 20 mmHg, such that the stomach is distended and determining the volume response; maintaining the distension pressure in the stomach for a specified period of time until a maximum volume is reached and determining the volume response; lowering the pressure in the balloon to the start minimum pressure and measuring the volume response; and comparing the volume response of the test human and a control human not having functional dyspepsia, wherein a reduction in the maximum gastric accommodation capacity of the test human compared to the maximum gastric accommodation capacity of the control human is indicative that the test human has functional dyspepsia. In one embodiment, the start minimum pressure is 1 mmHg. In another embodiment, the maximum pressure is 12 mmHg. In yet another embodiment the maintained distension pressure is 12 mmHg.

By the term "maximum gastric accommodation capacity" it is meant the velocity of adaptive accommodation of the stomach. It can be calculated by determining the increase in volume during the tonic phase of distension and the time needed to reach the maximum gastric volume.

By the term "impaired maximum gastric accommodation capacity" it is meant a maximum gastric accommodation capacity where the accommodation velocity of the stomach is found to be substantially less (e.g., more than two fold less, e.g., five fold, ten fold, etc) than that found in a control animal.

By the term "accommodation" it is meant the adjustment of the volume of the stomach, e.g., contraction or expansion, in response to a change in pressure, or a change in content.

By the term "control human" it is meant a human that does not have functional dyspepsia.

By the term "treatment" it is meant a means of obtaining a desired pharmacologic and/or physiologic effect. The effect may be prophylactic in terms of completely or partially preventing FD, or a symptom thereof, and/or may be therapeutic in terms of a partial or complete cure for FD, and/or adverse effect attributable to FD.

BRIEF DESCRIPTION OF THE FIGURES

FIG. 4(a) depicts a pressure volume curve of Sprague Dawley rats (SPDR) and healthy volunteers and FIG. 4(b) shows a pressure volume curve of Wistar Kyoto (WKY) rats and patients diagnosed with functional dyspepsia.

DETAILED DESCRIPTION OF THE INVENTION

Figure 1:
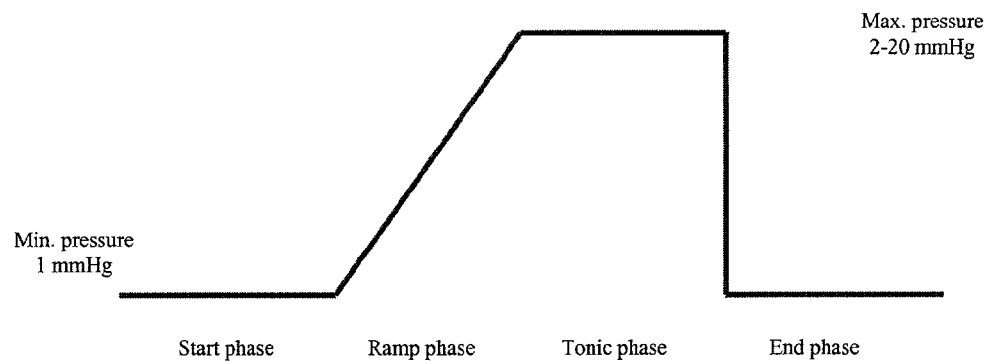
FIG. 1 depicts the four phases of the distension protocol.

FD is a chronic, recurrent, often meal-related epigastric disorder. It is a disorder of unknown aetiology and diagnosis is often made by the pattern of symptoms presented by an FD patient. Symptoms include nausea, vomiting, bloating, early satiety and epigastric pain. At present, doctors prescribe a large number of different agents alone, or in combination, to treat FD. Because there is no objective parameter for determining the efficacy of an agent, the only means to assess a drug's efficacy is to determine its effects on relieving the symptoms in the patient. Examples of drugs used to treat FD include antacids, antisecretory agents, prokinetics, mucosal protective agents, bismuth, anticholinergics, alginates, anti-foams, peppermint oil, herbal medication, tranquillisers\antidepressants or antibiotics. However, none of these drugs provide efficient treatment.

The invention described herein is based on the finding that a particular rat strain, Wistar Kyoto (WKY), exhibits a similarly impaired accommodation velocity in response to gastric distension as a patient with FD. The invention thus provides an animal model of human FD and a method for evaluating candidate agents which can be used to prevent or treat the development of FD. Moreover, this animal model finally provides an accurate means by which drugs can be objectively assessed by measuring the parameter of maximum gastric accommodation capacity (U).

Method to Identify a Candidate Agent for the Treatment of FD

The present animal model provides a convenient and easy way to determine the efficacy of a candidate agent. In order to evaluate if a candidate agent is useful in the treatment of FD, an agent of interest is administered to a non-human animal, e.g., a rat, dog, etc., that has been identified using the distension protocol described herein to have an impaired maximum gastric accommodation capacity.

Any non-human animal having an impaired maximum gastric accommodation capacity is suitable for use in the evaluation of the candidate compound. The suitability of the animal can be readily determined by one skilled in the art using the distension protocol. One suitable animal is the WKY rat. This rat strain, which was originally inbred to serve as a model for anxiety and depression, is known to suffer from stress (Solberg et al American Journal of Physiology—Regulatory Integrative & Comparative Physiology. 281(3):R786–94, 2001). Interestingly, stress is considered to be a major contributing factor in the development of FD. Based on this link, it can be envisaged that any animal which suffers from chronic stress may be suitable for the method, and a determination of its maximum gastric accommodation capacity can be routinely made as described herein.

The term "agent" as used herein describes any molecule, e.g. protein or pharmaceutical, with the capability of altering maximum gastric accommodation capacity, i.e., accommodation velocity. For example, the agent can include synthetic molecules such as small molecule drugs, or other synthetically produced molecules or compounds. The term agent also includes peptides, recombinantly produced gene products, and naturally-occurring compounds, e.g., polypeptides, endogenous factors, plant extracts, and the like. Examples of agents that can be tested include NO donors, NOS inhibitors, 5HT-3 agonists, 5HT-4 antagonists, alpha-2 agonists, glucagons, cholinergeric agonists or cholinergeric antagonists.

The candidate agent can be administered in any manner desired and/or appropriate for its delivery. For example, the candidate agent can be administered by injection (e.g., by injection intravenously, intramuscularly, subcutaneously, or directly into the tissue or organ of interest, e.g., the stomach), orally, or by any other desirable means. The in vivo screen can involve a number of animals receiving varying amounts and concentrations of the candidate agent (e.g., from no drug (control) to an amount of drug that approaches an upper limit that can be delivered successfully to the animal), and may include delivery of the drug in different formulations. The agent can be administered singly or in combinations with two or more agents, especially where administration of a combination of agents may result in a synergistic effect. The agent can be administered a few hours before the effect of the drug on maximum gastric accommodation capacity is monitored in the animal, or can be administered a few days before the determination is made. The drug could be administered as a single dose or as repeated doses.

Distension Protocol

In order to determine an animal's maximum gastric accommodation capacity, a balloon is inserted into the stomach of the animal and a four phase protocol which includes a start phase, a ramp phase, a tonic phase and an end phase is performed (see FIG. 1). The pressure applied to the balloon and the corresponding changes to the volume of the balloon are monitored throughout, e.g., using any barostat system known in the art (e.g., see Toma et al, Neurogastroenterol. Mot., 8, 19–28, 1996)

During the start phase a minimum distension pressure, e.g., 1 mmHg, is applied to the balloon until base line values are obtained. This is followed by a Ramp Phase. During this phase the pressure applied to the balloon is increased linearly with a constant increase in pressure. The pressure delivered to the balloon can be between 2–20 mmHg. This phase is then followed by the Tonic Phase. During the tonic phase the pressure is kept constant at the maximum pressure. Finally the pressure is dropped to the starting minimum distension pressure and this period is known as the End Phase (see FIG. 1).

Figure 2:
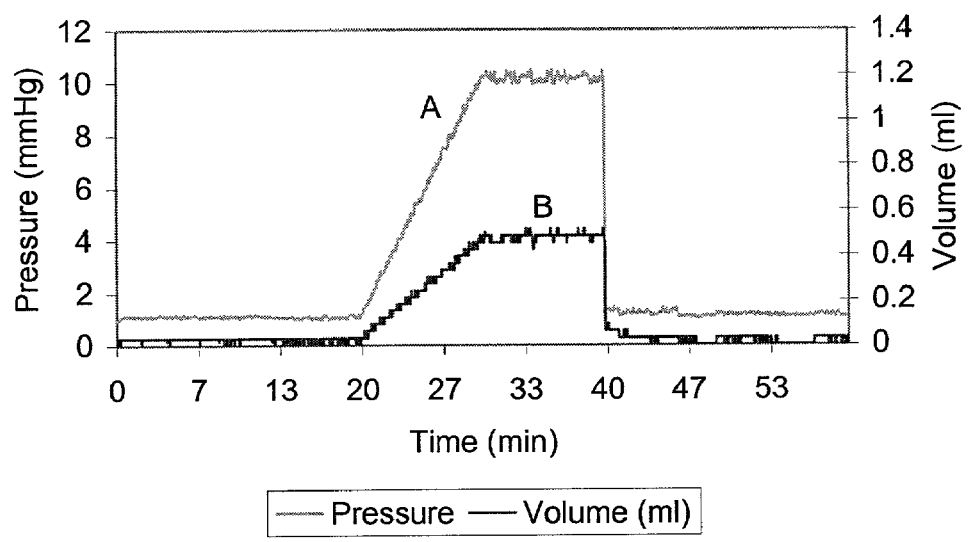
FIG. 2 depicts a typical pressure volume curve in an animal with impaired maximum gastric accommodation capacity. The pressure is represented by (A) and the volume is represented by (B).
Figure 3:
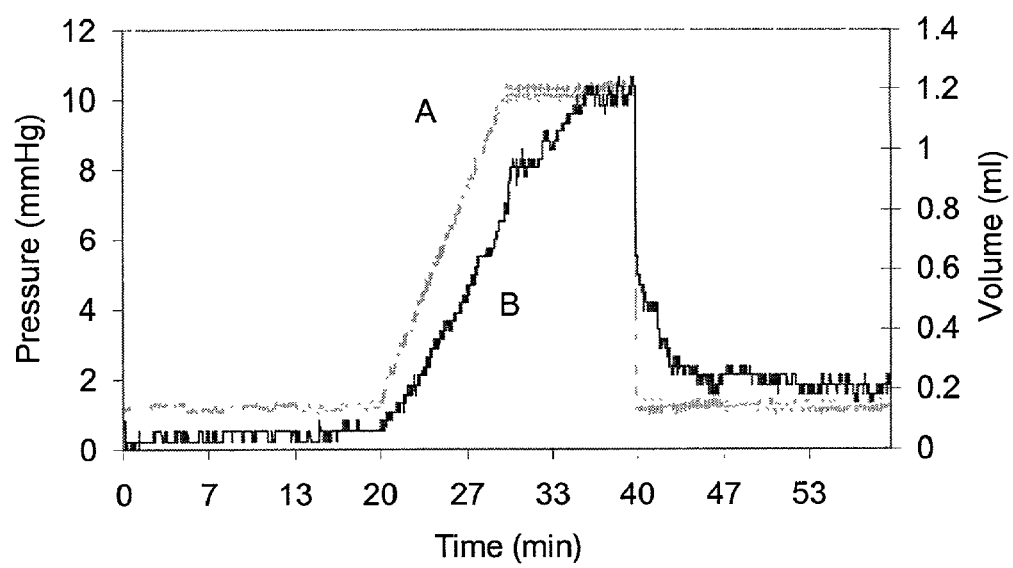
FIG. 3 depicts shows a typical pressure volume curve in a control animal with normal maximum gastric accommodation capacity. The pressure is represented by (A) and the volume is represented by (B).

Volume and pressure data are then analysed and data is plotted as curves. For example, FIG. 2 shows a typical pressure volume curve in an animal with impaired maximum gastric accommodation capacity and FIG. 3 shows a typical pressure volume curve in a control animal with normal maximum gastric accommodation capacity. The pressure is represented by (A) and the volume is represented by (B) in both figures.

As shown in the example section, when the distension protocol outlined above was performed on WKY rats and patients having FD, a significantly lower accommodation velocity was observed during the tonic phase when compared to controls. (The control for the rat is the Sprague Dawley rat and the control for the dyspeptic patient is a person not having FD). The accommodation velocity is calculated by measuring the slope of the curve during the tonic phase and this is referred to as the "maximum gastric accommodation capacity" or simply as "U".

While not wishing to be bound by theory, applicants believe that the physiological explanation for why during the Tonic phase the volume in the stomach increases despite the fact that the pressure is constant may be because the stomach continues relaxing during this tonic phase. In order for the barostat to keep the pressure constant it needs to pump more air into the stomach. The total volume change during the tonic phase thus represents the adaptive accommodation of the stomach and the slope of this increase (U) represents the maximum gastric accommodation capacity of the stomach. The results obtained using the distension protocol outlined herein show that the maximum gastric adaptive accommodation is significantly lower in WKY rats and Functional dyspeptic patients compared to Sprague Dawley rats, and persons not diagnosed FD, respectively. Even more interestingly, our studies have shown that the pressure volume curves of the WKY rats and Functional dyspeptic patients are very similar (see FIGS. 4a & 4b).

By measuring the maximum gastric accommodation capacity we have the opportunity to study the cause of volume change. This makes it finally possible to study the direct effects of pharmacological agents on the change in accommodation velocity. Thus, this model provides a means of being able to determine if a candidate agent can improve the gastric volume.

To determine if an agent, e.g., a compound is useful in the treatment of FD, the maximum gastric accommodation capacity in the animal following administration of the compound is calculated. A compound of interest will be a compound that alters the maximum gastric accommodation capacity in the animal and this is calculated by determining a difference in the maximum gastric accommodation capacity before and after administration of the compound.

Identified Candidate Compound

The compounds having the desired activity may be administered in a physiologically acceptable carrier to a functional dyspeptic patient. The identified candidate compound may be administered in a variety of ways, orally, topically, parenterally, e.g., subcutaneously, intraperitoneally, by viral infection, intravascularly, etc. Depending upon the manner of introduction, the compound may be formulated in a variety of ways. The concentration of the therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and use can be used to make up compositions containing the therapeutically-active compounds.

Diluents known to the art include aqueous media, vegetable and animal oils and fats. Stabilizing agents, wetting and emulsifying agents, salts for varying the osmotic pressure or buffers for securing an adequate pH value can be used.

Method for the Determination of FD in Humans

The present invention also provides an accurate and simple method for determining if a patient has FD by using the distension protocol described herein.

The accompanying Figures and the following Examples support and illustrate the claimed invention.

EXAMPLE

The aim of the present study was to determine if a distension model in a rat stomach had similar physico-mechanical properties to those of the stomach of a patient with FD.

Example 1

Gastric Distension and Volume Recording in Rats 1.1: Distension Protocol in Rats:

A combination of ramp and tonic distension was used in all the experiments. The protocol starts with a minimum distension pressure of 1 mmHg and continues for 20 min in order to collect base line values. The pressure is then increased by a velocity of 1–4 mmHg/min for 10 min to a maximum pressure of 10–20 mmHg (ramp phase). The barostat then keeps the pressure at the maximum pressure for 10 more min (tonic phase). After the tonic phase the pressure drops to the minimum distension pressure of 1 mmHg in about 1 s. The pressure is then kept at this level for another 20-minute period (see FIG. 1).

1.2: Gastric Distension and Recording

The Wistar Kyoto rats (WKY; M&B Denmark) and Sprague Dawley rats (SPDR) were starved about 8 or 18 hours before each experiment depending on if the experiments were performed in the morning or in the afternoon. A small, inflatable balloon was inserted through the central hole of the fistula into the distal part of stomach under isoflurane anaesthesia (Forene®, Abbott Scandinavia AB) and was fixed in its position through the tightening of the fistula. The balloon had a spherical shape with a wall thickness of about 15 $\mu$m, a non-distensible max diameter of 25 mm and a max volume of about 7 ml. The balloon was connected to a double-lumen polyethylene catheter with an outer diameter of 1.40 mm and a length of about 20 cm. The inner lumen diameter of the catheter was about 0.58 mm. The animals were placed in a specially designed Bollmann cage, with an inner diameter of 60 mm for females and 70 mm for males. The catheter was then, via a pressure transducer, connected to a barostat system.

A barostat system maintains the pressure by pumping air into and out of the balloon. After the experiment the balloon and the connecting cable were removed under isoflurane anaesthesia and the animals were returned to their normal cages.

1.3 Results

Volume and pressure data were analysed and plotted. The volume curve was divided into four different parts:
1) Start phase: From the beginning of the curve to the start of the ramp phase.
2) Ramp Phase: From the start of the ramp phase of the pressure curve to the start of the tonic phase of the pressure curve.
3) Tonic phase: The volume curve during the tonic pressure phase.
4) End phase: The part of volume curve after the tonic phase.

Figure 5:
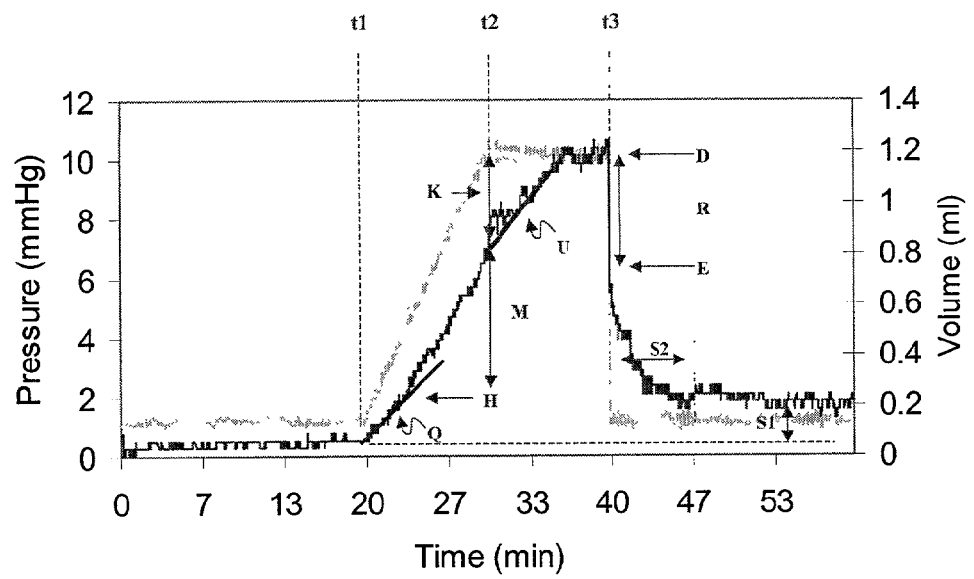
FIG. 5 depicts a pressure volume curve showing different measurable parameters.

Different parameters were calculated (see FIG. 5). Parameters were:

Q=basal tone of the stomach (ml/s). This represents the elasticity of the stomach.

H=threshold point when the stomach starts relaxing in response to increased pressure/volume.

Hp=pressure at threshold (mmHg)

Hv=volume at threshold (ml)

T=time to threshold (s).

M=accommodation during increasing pressure (ml). This is the volume change from Hv to volume at start of tonic distension phase.

K=accommodation during constant pressure (ml). This is the volume change during the tonic phase.

U=maximum gastric accommodation capacity (ml/s). This is the increase of volume in ml/s during constant pressure.

D=maximum volume (ml)

R=elastic property of the stomach during decreasing pressure (ml). This is the volume decrease caused by rapid decrease in pressure.

S1=hysteresis (ml). This is the difference in volume between the volume at minimum distension pressure after distending the stomach and the volume at minimum distension pressure before distending the stomach.

S2=time to S1 (s).

X=balloon diameter (mm).

Start phase: This was the volume producing a pressure of 1 mmHg in the stomach before any distension.

Ramp phase: The part of the volume curve from the start of the ramp phase to the start of the tonic phase showed a bi-phasic profile with two distinct slopes in the beginning and at the end of the curve. This curve was fitted to two straight lines using an iteration process and the deflection point (H) of the curve was calculated. The slope of the first part of this curve was also calculated (Q). The volume change from the defection point up to the end of this part of the volume curve was measure and will be referred to as (M).

Tonic phase: This part of the volume curve showed an increasing profile until it reaches a plateau at the end of this part of the curve. The slope of the increasing part of the curve was calculated and will be referred to as (U). The total increase of the volume during this period was also measured and will be referred to as (K). The maximum volume during this period is the maximum volume during the experiment and will be referred to as (D).

End phase: This part of the curve showed also two different patterns. At the beginning when the pressure drops fast to a minimum distension pressure of 1 mmHg the volume drops to a value assigned as (R). After this point the volume decreases exponentially to a value of (S1). It will take the volume curve (S2) seconds to drop to this level.

Figure 6:
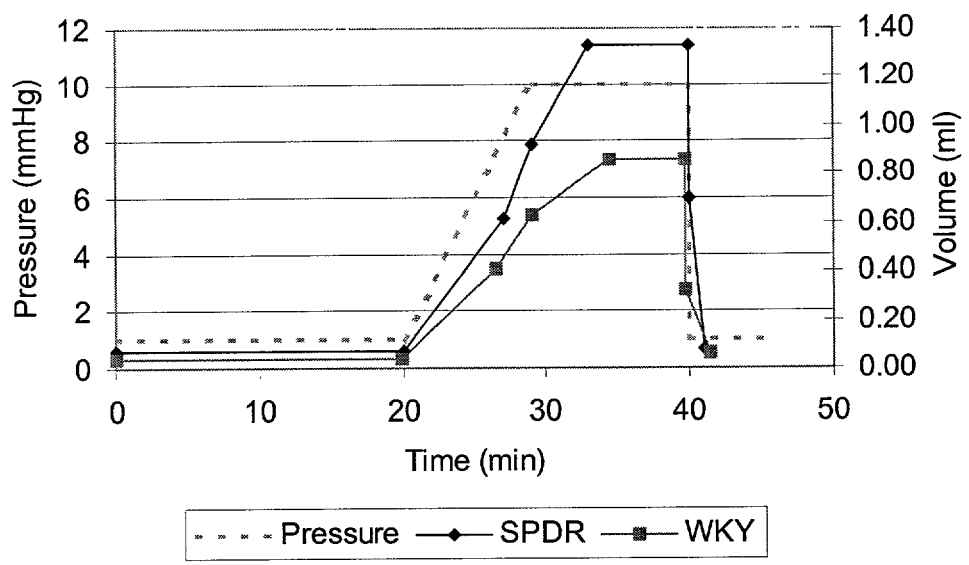
FIG. 6 depicts a pressure volume curve obtained for a SPDR and WKY rats.

In the rats the mean gastric volume of the SPD rats with a maximum pressure of 10 mmHg was measured to $1.33 \pm 0.1$ ml which was significantly larger than that of the WKY rats $0.86 \pm 0.06$ ml (p=0.001). Maximum gastric accommodation capacity in the two rat strains was calculated to 6.7e-$4 \pm 6.6$e-5 vs 4.2e-$4 \pm 3.0$e-5 (p<0.001, FIG. 6).

Example 2

Gastric Distension and Volume Recording in Humans 2.1 Protocol for Gastric Distention in Humans Ten healthy subjects and ten dyspeptic patients diagnosed according to Rome II criteria were used in the studies. After an overnight fasting a finely folded plastic balloon with a maximum non distensible volume of 1200 ml connected to a double lumen catheter was inserted orally into the stomach and was fixed at about 55 cm from the chin.

The test subject was then placed in a comfortable chare leaning backwards. The catheter was connected to a specially designed barostat and the system was initialised.

During the initialisation process the balloon was completely emptied and then the pressure of the balloon was increased to 4 mmHg in order to open the folded balloon. The pressure was then decreased to one mmHg which is the minimum pressure used in the study. The volume of the balloon was measured. Twenty minutes after the initialisation process the experiment was started. The pressure and the volume data were continuously collected and saved for twenty minutes in order to collect the base line values. The pressure in the balloon was then increased gradually to a maximum pressure of 12 mmHg during 4 minutes i.e. an increasing velocity of 3 mmHg/min. At this time the pressure in the balloon was kept constant at 12 mmHg for 5 minutes where after the pressure was decreased to one mmHg and was kept for another 20 minutes. During the whole experiment the pressure and the volume were measured continuously and saved digitally. At the end of the experiment the balloon was tested for leakage.

2.2 Results

Figure 7:
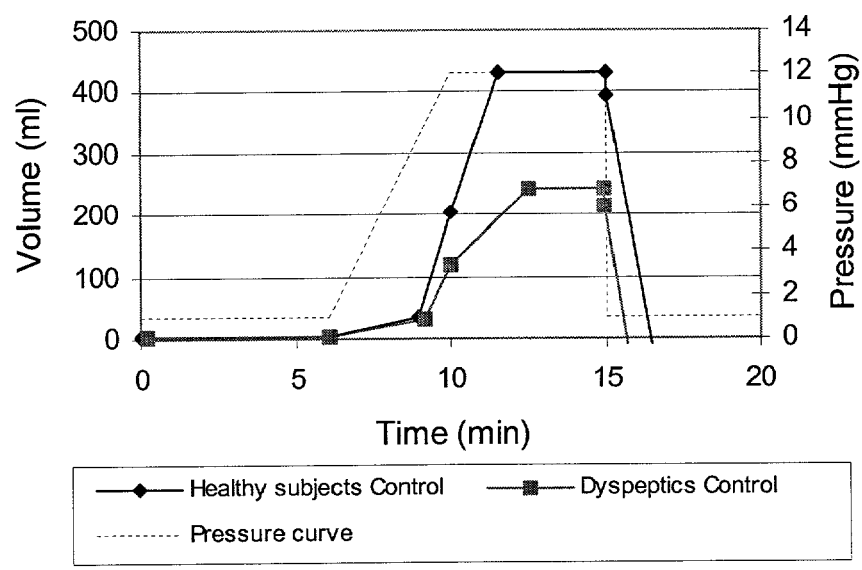
FIG. 7 depicts a pressure volume curve obtained for healthy humans and functional dyspeptic patients.

The mean maximum gastric volume of the healthy subject group with a pressure of 12 mmHg was measured to $428 \pm 64$ ml. This value was significantly greater than the corresponding value measured in the dyspeptic group $244 \pm 43$ ml (p=0.02). The maximum accommodation capacity in the control healthy subject group was calculated to be $2.43 \pm 0.4$ ml/s which was significantly larger than the corresponding value calculated for the dyspeptic group $0.83 \pm 0.15$ (p=0.003, FIG. 7).

2.3 Physiological Explanation of the Volume Curve:

During the first phase of the curve the pressure in the stomach is constant (1 mmHg) and the barostat will not pump in any air into the stomach, that is if the stomach does not relax. During this period the amount of air pumped into or drawn out of the stomach is solely dependent on the relaxation or contraction of the stomach.

During the ramp phase the barostat will infuse air into the stomach even if the stomach does not relax until the preset pressure is reached. The volume pumped during this period is dependent on the activity of the barostat, which wants to increase the pressure and the relaxation or contraction of the stomach.

During the tonic phase the pressure in the stomach is constant that means the barostat will not actively pump in air into the stomach. Air will however be pump into the stomach if the stomach relaxes and air will be pulled out if the stomach contracts in order to keep the pressure constant.

At the beginning of the ramp period when the barostat starts increasing the pressure in the stomach the velocity of the infused pump is dependent on, among other things, the elasticity of the stomach. That is, the more compliant the stomach is the larger amount of air will be needed to increase the pressure to a constant level. This property of the stomach can be soon in the deflection point of the volume curve. As the pressure and/or volume increase it reaches a level where the stomach starts relaxing. The barostat, then, in order to be able to increase the pressure linearly as preset, will increase the velocity of the influent air into the stomach as can be seen in the change in the velocity (slope) of the second part of the volume curve. It must be mentioned that even though in this context we refer to the deflection point as "a point" it does not mean that in reality it is a single point where the relaxation starts. This point is merely a reflection of a measurable point of the start of the relaxation of the stomach.

The slope of the first part of this curve (Q) will then represent the elasticity of the stomach. The information during the active barostat period, i.e. during the second part of the curve, is much more complicated as there are two different processes (infusion of the air into the stomach to increase the pressure by the barostat, and the relaxation of the stomach) working together.

At the deflection point one can measure the volume (Hv) and the pressure (Hp) in the stomach as levels starting the relaxation process in the stomach.

During the Tonic phase the volume in the stomach increases despite the fact that the pressure is constant (Passive barostat period). The only explanation for this is that the stomach continues relaxing during this tonic phase and in order for the barostat to keep the pressure constant it needs to pump more air into the stomach. This is true if the system does not leak. This aspect is checked always before and after each experiment and a very good indicator that leakage is not the reason for the increase in the volume of the stomach during the tonic phase is the fact that the volume always reaches a maximum and plateaus at that volume. The total volume change during the tonic phase (K) represents the adaptive accommodation of the stomach and the slope of this increase (U) represents the maximum gastric accommodation capacity.

When the pressure drops to the minimum distension pressure of 1 mmHg after the tonic phase the gastric volume does not decrease to its value before the distension. The volume decreases to a level dictated by the elasticity of the stomach. The value (R), then, represents the elasticity of the stomach.

During the few minutes after the tonic phase up to (S2) the contraction of the muscles of the stomach results in a total emptying of the stomach reaching to a volume of (S1). This volume is, however, higher than the volume of the stomach before the distension. This difference represents the hysteresis phenomenon seen in the stomach. Given enough time this volume will eventually reach the normal volume of the stomach seen before the distension.

What is claimed is:

1. A method of identifying a test compound useful for the treatment of an impaired maximum gastric accommodation capacity, wherein the method comprises:
    administering a test compound to a non-human animal identified to have an impaired maximum gastric accommodation capacity;
    measuring the gastric accommodation during a ramp phase and during a tonic phase and determining from these measurements the maximum gastric accommodation capacity in the animal following administration of the compound; and
    comparing the maximum gastric accommodation capacity of the animal before and after administration of the test compound, wherein an increase in the accommodation capacity in the animal following administration of the compound is indicative that the compound is useful for the treatment of impaired maximum gastric accommodation capacity.

2. The method of claim 1, wherein the non-human animal is a rat or a dog.

3. The method of claim 2, wherein the rat is a Wistar Kyoto rat.

4. The method of claim 1, wherein the compound is a nitrogen oxide synthase (NOS) inhibitor, a 5HT-3 agonist, a 5HT-4 antagonist, an alpha-2 agonist, a glucagon or a cholinergic agonist or antagonist.

5. The method of claim 1 wherein the compound is administered orally.

* * * * *